(12) United States Patent
Shpantzer et al.

(10) Patent No.: US 8,019,556 B2
(45) Date of Patent: *Sep. 13, 2011

(54) INSPECTION SYSTEM AND METHOD

(76) Inventors: Isaac Shpantzer, Bethesda, MD (US);
Yaakov Achiam, Rockville, MD (US);
Nadejda Reingand, Baltimore, MD (US)

( * ) Notice: Subject to any disclaimer, the term of this patent is extended or adjusted under 35 U.S.C. 154(b) by 228 days.

This patent is subject to a terminal disclaimer.

(21) Appl. No.: 12/539,484

(22) Filed: Aug. 11, 2009

(65) Prior Publication Data

US 2009/0295576 A1    Dec. 3, 2009

Related U.S. Application Data

(63) Continuation of application No. 11/626,920, filed on Jan. 25, 2007, now Pat. No. 7,652,254, and a continuation-in-part of application No. 10/947,640, filed on Jan. 13, 2005, now Pat. No. 7,277,178.

(60) Provisional application No. 60/883,420, filed on Jan. 4, 2007.

(51) Int. Cl.
*G01T 1/00* (2006.01)
*G01J 3/45* (2006.01)

(52) U.S. Cl. ........... 702/23; 702/22; 702/28; 250/358.1; 250/307; 250/397; 356/451; 340/539.26; 340/539.29; 340/600

(58) Field of Classification Search ............... 250/358.1, 250/251, 306–308, 336.1, 390.01, 397; 340/600, 340/539.26, 539.29; 356/451, 432, 484, 356/517; 702/22, 23, 28, 30
See application file for complete search history.

(56) References Cited

U.S. PATENT DOCUMENTS

| 4,670,656 | A * | 6/1987 | Bolon ........................ 250/385.1 |
| 6,965,314 | B2 * | 11/2005 | Bohinc, Jr. ............... 340/539.26 |
| 7,015,475 | B2 * | 3/2006 | Hailey ........................ 250/358.1 |
| 7,151,447 | B1 * | 12/2006 | Willms et al. ................. 340/540 |
| 7,277,178 | B2 * | 10/2007 | Shpantzer et al. ............ 356/451 |
| 7,470,905 | B1 * | 12/2008 | Goldberg et al. .......... 250/358.1 |
| 7,488,934 | B2 * | 2/2009 | Bryman ........................ 250/266 |
| 7,652,254 | B2 * | 1/2010 | Shpantzer et al. ............ 250/307 |
| 7,838,841 | B2 * | 11/2010 | Morris et al. ................. 250/397 |
| 2006/0284094 | A1 * | 12/2006 | Inbar ......................... 250/359.1 |
| 2008/0228418 | A1 * | 9/2008 | Green ............................. 702/81 |
| 2008/0315091 | A1 * | 12/2008 | Morris et al. ................. 250/307 |

OTHER PUBLICATIONS

Hengartner et al, Information Extraction for Muon Radiography, IEEE, Nuclear Science Symposium Conference Record, Nov. 2005, N1-5.*

* cited by examiner

*Primary Examiner* — George Bugg
*Assistant Examiner* — Anne Lai

(57) ABSTRACT

A method and system for nuclear substance revealing using muon detection technique is presented. In some aspects, naturally occurred muons are selected from the flow of charged particles. Muon coordinate and incidence angle measured above and below the interrogated volume can be used for the decision making on the presence of nuclear substance inside the volume. The system is adapted for performing measurements on moving objects such as moving trucks. A combination of the nuclear substance detection system with an explosive sensing system is presented.

20 Claims, 6 Drawing Sheets

INSPECTION SYSTEM AND METHOD

CROSS-REFERENCE TO RELATED APPLICATIONS

The present invention claims the benefit of U.S. Ser. No. 60/883,420 filed Jan. 4, 2007 and is also a continuation of Ser. No. 11/626,920 filed Jan. 25, 2007 now U.S. Pat. No. 7,652,254 and a continuation-in-part of U.S. Ser. No. 10/947,640, filed Jan. 13, 2005 now U.S. Pat. No. 7,277,178, which are fully incorporated herein by reference.

FIELD OF INVENTION

This invention relates generally to the systems and methods for revealing of uranium, plutonium and other dense materials using muon detection technique.

BACKGROUND OF THE INVENTION

Flow of cosmic rays constantly bombards Earth. Primary cosmic rays consist of single protons (about 90% of all cosmic rays) and alpha particles (majority of the remaining 10%). When these primary cosmic rays hit Earth's atmosphere at around 30,000 m above the surface, the impacts cause nuclear reactions, which produce pions. These pions decay into a muon and muon neutrino at about 9000 m altitude. Many muons decay on the way down into neutrinos and an electron while others reach the surface, and there are still enough particles to be detected fairly easily. About 10,000 muons rain down on each square meter of Earth every minute. This flux is approximately uniform over the Earth's surface.

Muons are electrically charged unstable elementary particles with a mean energy of about 4 GeV, which rain down upon the surface of the earth, traveling at about 0.998 c, where c is a speed of light. The muon has an average half-life of $2.2 \cdot 10^{-6}$ s. The angular distribution of the muons is proportional to $\cos^2 \alpha$, where a is calculated from the vertical direction.

Muon flow can also be generated artificially. U.S. Pat. No. 3,970,936 discloses communications line that employs such muon source. According to U.S. Pat. No. 7,015,475 current size of accelerators for muon generation can be as small as room-size.

Various detection techniques were proposed for muons detectors. Muon detectors described below are presented here for the purpose of proof of the systems feasibility. However it does not limit the concept of the present invention to this particular type of detectors.

Cloud chambers with supersaturated vapor can be named as the most popular type of detectors. Cloud chambers allow visualization of muon trajectory. If the chamber is equipped with a three-dimensional coordinate system, the muon incident angle and coordinate can be measured.

The most suitable types of muon detectors for the current system are wire chambers and drift chambers (http://universe-review.ca/I15-02-wirecounter.jpg). The wire chambers consist of very large number of parallel wires, where each wire acts as an individual detector. A particle leaves a trace of ions and electrons, which drift toward the nearest wire. By marking off the wires which had a pulse of current, one can see the particle's path. Several planes of wires with different orientations are used to determine the position of the particle very accurately. A drift chamber has a similar construction shown in FIG. 1. Typically the chamber has two windows 1 and 2, where 1 is a mylar window. Gas pump 3 is connected with the chamber by inlet and outlet pipes 4 and 5. Three wire gratings are inserted between the windows: two cathode wire planes 6 and 7 and a sense wire plane 8 located in between. The wires in the sense plane spaced farther apart than the wires of the cathode gratings. Output 9 yields a signal caused by a muon passing through the chamber. Varying voltages applied from the source 10 to the cathode wires produce a field in which ionization electrons drift at a constant velocity towards the nearest sense wire. The drift time, measured by an electronic "stopwatch" started by a signal from a scintillator 11, is directly related to the distance between the track of the particle and the wire that produces a signal. This greatly increases the accuracy of the path reconstruction.

The coordinate resolution in best muon detectors (such as drift tubes) can be as good as 50 micrometers.

Additionally, a scintillation detector may be used for muon sensing. Such detector has a good spatial resolution. They can be made by forming layers of plastic optical fibers made out of scintillator material coated with a lower refractive index cladding. These can typically have a diameter of 0.5 to 1 mm. The small size of each independent scintillator means that many readout channels (typically tens of thousands) are required, and it is not practical to equip each one with its own photomultiplier. One solution to this is to gather the fibers into a bundle and connect to an image intensifier. This amplifies the light while maintaining an image, which can then be viewed with a CCD camera, and the position on the image associated with a particular fiber.

Since other particles are stimulating the detector as well, a system of two detectors was proposed to avoid false muon detection. Other particles originating from i.e. terrestrial radiation will also cause stimulation, but those particles have too less energy to penetrate both detectors. They will end up either in the first detector or shortly after it. The detection that occurs almost instant in both detectors is considered as a successful detection of a muon. Muons shielding is not limited to above mentioned additional detector; any other types of shielding can be in order to separate muons from other charged particles.

A sandwich of two coordinate detectors located along the muon path allows simultaneous detecting both the incident angle of the muon and it's coordinate. An ensemble of three detectors allows selecting muons and measuring their coordinates and incident angles.

It is known that muons easily penetrate most of the materials. However an increase of the muon deflection is observed when they pass materials with high atomic number Z such as nuclear or gamma-ray-shielding materials. Two materials that can be used to make an atomic bomb: plutonium-239 and highly enriched uranium with at least 20 percent of uranium-235. Since both materials have high Z numbers, both can be detected by muon technique. Probability of muon deflection angle forms a Gaussian function with a zero mean angle and a width that depends on the material Z number. While muon deflection in 10 cm of aluminum is up to about 10 milliradians, it reaches a value of about 80 milliradians in uranium and plutonium (about 10 cm thick specimen).

Current technologies for nuclear material detection are limited to X-ray and Gamma ray equipment. Both systems must be accurately handled, and their emissions properly controlled. There is a need for reliable and safety system to unveil hidden nuclear materials. Muon detection technique provides a safety alternative with improved penetration ability.

Security check point with muon detector may be combined with other sensor equipment. There is a need for simultaneous check of hidden explosives and nuclear materials at the security check point.

SUMMARY OF THE INVENTION

The system and method are disclosed for nuclear materials detection by muon flow sensing. The system comprises a shielding layer for muons selection and a series of muon sensors positioned in three dimensional space for efficiently detecting muons deflection caused by the presence of high Z materials.

In the preferred embodiment the measurement is performed when a vehicle or container with said material passes through the space surrounded by detectors.

The detectors may be manufactured being hidden or camouflaged in the environment.

In the preferred embodiment a trajectory of each particular muon is measured and the data serves for nuclear material revealing.

The electrical output signals from the detectors are processed in DSP unit connected to an alarm system to produce a signal if the presence of nuclear material is suspected inside the interrogated volume.

DETAILED DESCRIPTION OF THE PREFERRED EMBODIMENT

Figure 1:
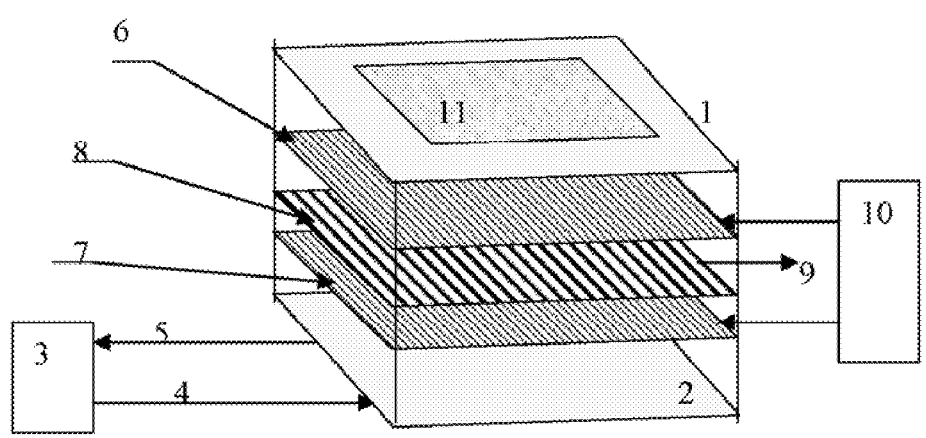
FIG. 1 Muon detector (Prior art).
Figure 2:
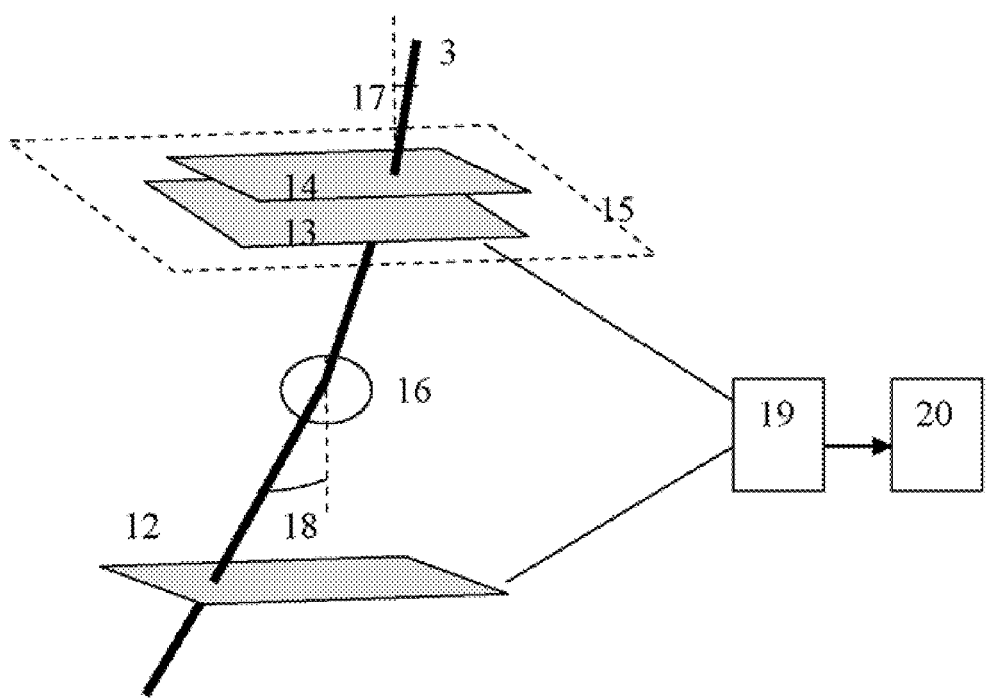
FIG. 2 System for measurement of muon deflection caused by nuclear material.

In one embodiment of the present invention, a series of muon sensors is proposed as shown in FIG. 2 (a). In the preferred embodiment one sensor 12 is positioned below the interrogated area, for example, on the ground or under the ground. Similar muon sensor 13 with a shielding layer 14 is positioned above the ground level. An ensemble of the sensor 13 and the shielding layer 14 is numbered 15. Each of the sensors 12 and 13 allow measuring the muon incidence angle with an accuracy of at least 1 milliradian and muon coordinate with an accuracy of at least 1 millimeter. In the absence of high Z material between sensors 12 and 13 the muon incidence angle is the same for sensors 12 and 13. In the presence of high Z material 16 a muon deflection is observed. The incidence angle 17 at the top sensor 13 differs from the incidence angle 18 at the bottom sensor 12. Each sensor constantly registers flow of muons passing through. Coordinate and incidence angle for each muon are measured at the top sensor 13. These data is used in Digital Signal Processing unit 19 to calculate the expected muon coordinate and incidence angle at the bottom sensor 12. Actual coordinate and angle are compared with the predicted parameters. An alarm system 20 generates an alarm if an essential deviation is observed. The predetermined value of the incident angle deviation that triggers the alarm depends on the type and size of objects under investigation. A predetermined trigger value of deviation may be chosen from 1 to 100 milliradian. In the preferred embodiment the predetermined trigger value of the deviation is 10 milliradian. Large size muon detectors must be used for the disclosed system. For example, a muon detector of at least 2 meter×3 meter square size must be used to detect hidden nuclear materials in cargo containers or trucks. The distance between the first and the second muon detectors may be from 10 cm to 5 meters.

Figure 3:
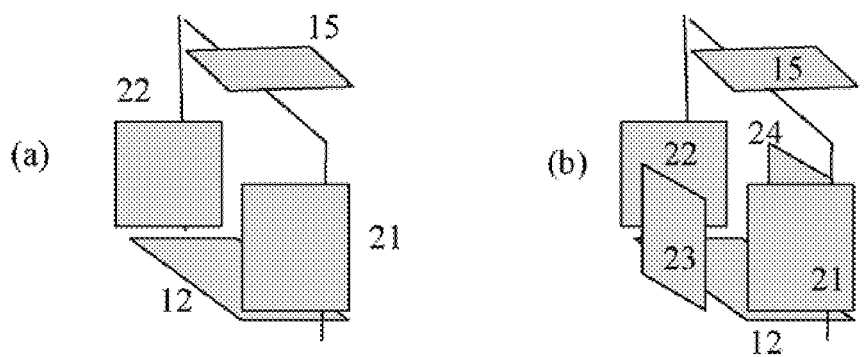
FIG. 3 (a) Three dimensional positioning of muon sensors in one series; (b) Series of detectors with additional side sensors.

Multiple series of sensors are arranged to form a three dimensional structures depicted in FIGS. 3 (a) and (b). U-shaped configuration shown in FIG. 3 (a) improves sensitivity of the detection. Introduction of vertical sensors 21 and 22 is equivalent to increasing of the bottom sensor square. Even larger increase of the sensitivity is achieved by additional vertical sensors 23 and 24 that form a box-like configuration shown in FIG. 3(b).

The vertical detectors 21, 22, 23 and 24 may be positioned at an angle from 0 to 90 degrees to the plane of the bottom detector 12. In the preferred embodiment the vertical detectors are positioned at an angle of 45 degrees to the bottom detector 12.

The suspicious container or vehicle is placed in between the top and the bottom detectors, and the muon deflection is measured. Alternatively the measurement is performed when a vehicle with the container moves through the system of sensors.

Figure 4:
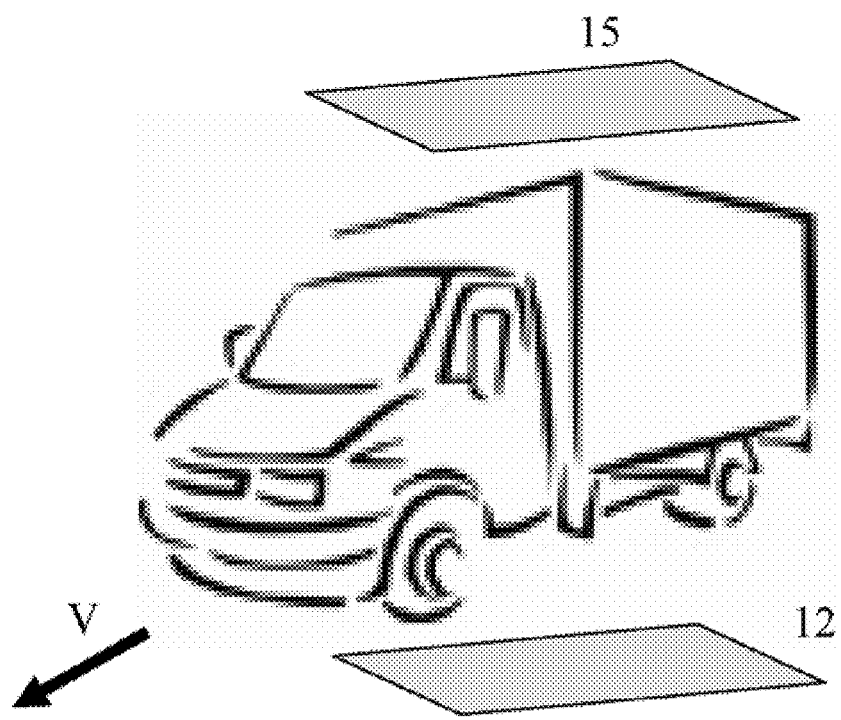
FIG. 4 A vehicle passing through the multiple series of muon sensors.

A vehicle passing through the system of muon sensors is shown in FIG. 4. Since the speed of muon essentially exceeds the speed of a moving truck, the truck motion does not affect the measurement of muon trajectory. The speed of the truck and the size of the detector must assure measurement of at least one muon trajectory in each square of 100 cm² of the truck surface, which is parallel to the ground. For example, for a 9 sq. meter detector (3×3), a vehicle moving at a speed of 10 km/hour guarantees measuring muon trajectories for each 100 cm² of its surface parallel to the ground. It is obvious that the detector of large size improves the accuracy of the measurement. A series of sensor systems positioned along the way of the vehicle improves sampling and thus reduces false alarm.

The detectors may be manufactured being hidden or camouflaged in the environment. The bottom sensor or U-shaped system of sensors may be positioned under the ground.

Figure 5:
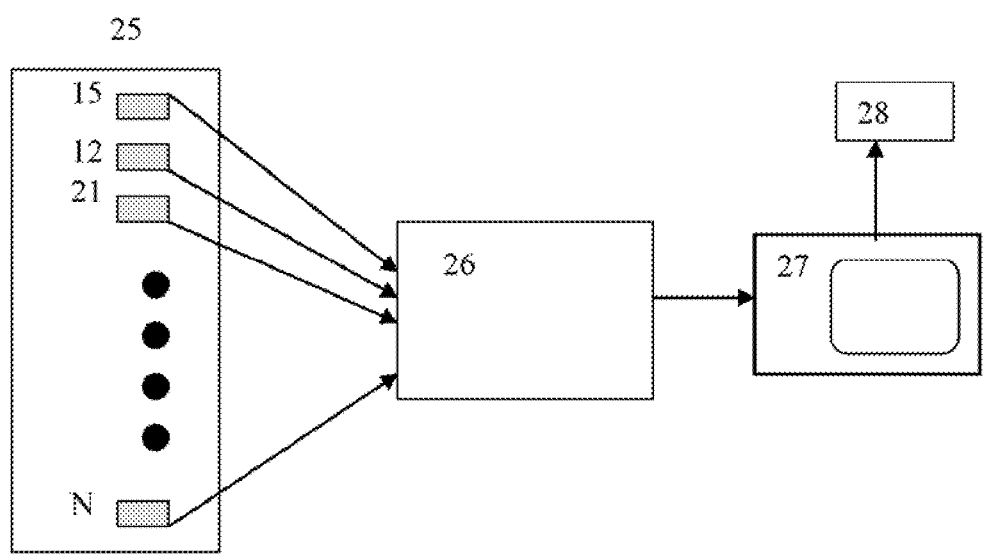
FIG. 5 Digital signal processing and display of data from multiple sensors.
Figure 6:
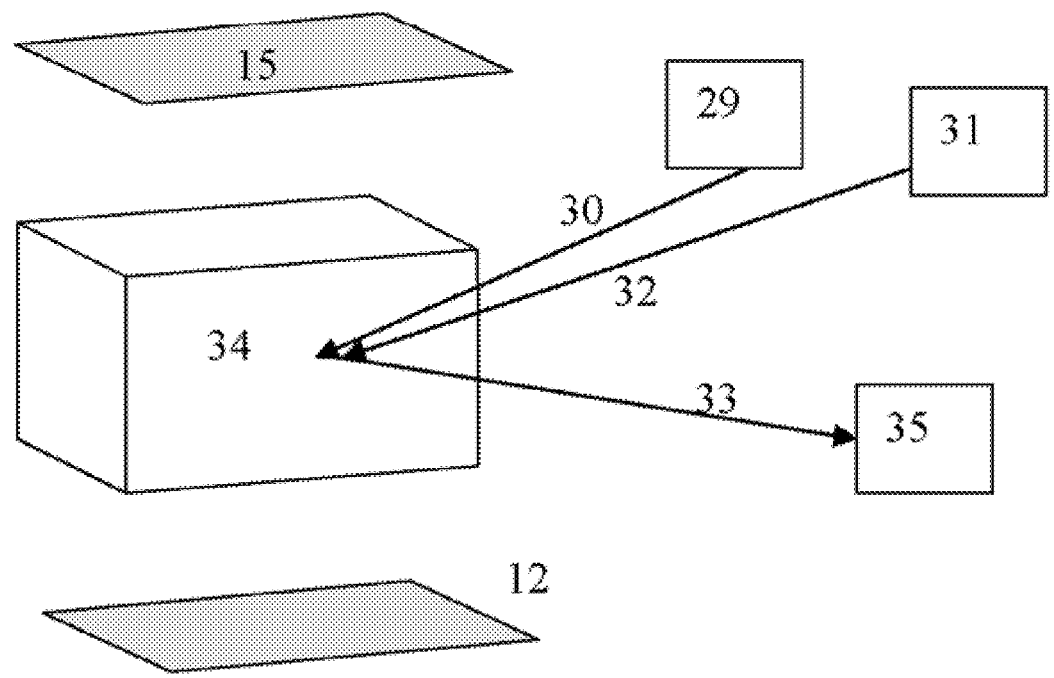
FIG. 6 Nuclear material revealing system combined with explosives detection system.

FIG. 5 depicts the processing of data from a number of sensors 12, 15, 21, 22 . . . N. The system 25 of sensors 12 . . . N registers spatial and temporal appearance of muons. Data from all sensors 12 . . . N enter digital signal processing (DSP) unit 26, where the trajectory of each particular muon is calculated and compared with the measured result. The results of the data analysis are shown on display 27. If the deviation of the measured parameter differs from the calculated one more than a predetermined value, an alarm 28 starts. The alarm 28 may be audible or visual alarm.

Security check point with muon detector may be combined with other sensor equipment. There is a need for simultaneous check of hidden explosives and nuclear material at the security check point.

US patent application No. 20050105099 discloses a photothermal, interferometric spectroscopy system that provides information about a chemical (such as explosive) at a remote location. A first light source assembly 29 emits a first beam 30 that interact with the chemical and change a refractive index of the chemical. A second light source 31 produces a second beam 32. The second beam 32 interacts with the chemical resulting in a third beam 33 after reflection from the surface 34. The third beam 33 experienced a phase change that corresponds with the change of the refractive index of the chemical. A detector system 35 is positioned remotely from to receive at least a portion of the third beam. The detector system provides information on a phase change in the third beam relative to the second beam that is indicative of at least one of, absorption spectrum and concentration of the chemical.

There is a need for a combination of two systems, one for hidden explosives detection and another for smuggled nuclear materials revealing, at the nuclear power plant security gates.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

The system allows fast detection of nuclear materials when the traffic passes through the detection area without stopping vehicles. The system can be installed on roads, in tunnels, in cargo station, in seaports and other locations. Toll stations could be convenient places for installations of such nuclear material detectors. The similar system of sensors may be installed at luggage transportation conveyor.

What is claimed is:

1. A system for nuclear material detection, comprising: a shielding layer adapted to allow muons, passing through the shielding layer while cutting off all other charged particles, at least a first flat muon detector and a second flat muon detector positioned along the way of muons passed through the shielding layer, the first muon detector is indicative of a first muon coordinate and a first incidence angle, and the second muon detector is indicative of an actual second muon coordinate and an actual second incidence angle, a digital signal processing unit for calculating a predicted second coordinate and a predicted second incidence angle, an alarm system being adapted for generating an alarm when a presence of a nuclear material between the first and the second flat muon detectors suspected, wherein the digital signal processing unit compares the actual second muon coordinate and the actual second incidence angle with the predicted second coordinate and the predicted second incidence angle for each muon, and the presence of nuclear material between the first and the second muon detectors is suspected if a difference between the actual second incidence angle and the predicted second incidence angle is larger than a predetermined value; further comprising: a chemical detection system, wherein the chemical detection system is a photo-thermal, interferometric spectroscopy system, including a first light source assembly that emits a first beam, the first beam having one or more wavelengths that interact with the chemical and change a refractive index of the chemical; a second light source that produces a second beam, the second beam interacting with the chemical resulting in a third beam with a phase change that corresponds with the change of the refractive index of the chemical; and a detector system positioned remote from the chemical to receive at least a portion of the third beam, the detector system providing information on a phase change in the third beam relative to the second beam that is indicative of at least one of, absorption spectrum and concentration of the chemical.

2. The system according to claim 1, wherein the first and the second flat muon detectors are essentially parallel.

3. The system according to claim 2, wherein the distance between the first and the second flat detectors is at least 2 meters in the direction perpendicular to the first and the second flat detectors.

4. The system according to claim 2, further comprising: a third muon detector and a fourth muon detector, wherein the third muon detector is indicative of the second muon coordinate and the second incidence angle, and the fourth muon detector is indicative of the second muon coordinate and the second incidence angle.

5. The system according to claim 4, wherein the third muon detector and the fourth muon detector are positioned at an angle from 45 degrees to 90 degrees relative to the first and the second muon detectors.

6. The system according to claim 4, wherein the third muon detector and the fourth muon detector are positioned essentially perpendicular to the first and the second muon detectors.

7. The system according to claim 4, further comprising: a fifth muon detector and a sixth muon detector, wherein the fifth muon detector is indicative of the second muon coordinate and the second incidence angle, and the sixth muon detector is indicative of the second muon coordinate and the second incidence angle.

8. The system according to claim 7, wherein the fifth muon detector and the sixth muon detector are positioned at an angle from 45 degrees to 90 degrees relative to the first, the second, the third and the fourth muon detectors.

9. The system according to claim 7, wherein the fifth muon detector and the sixth muon detector are positioned essentially perpendicular to the first, the second, the third and the fourth muon detectors.

10. The system according to claim 1, further comprising: a muon generation source that outputs moons to be detected by the first and the second muon detectors.

11. The system according to claim 1, wherein the first and the second muon detector both have coordinate resolution of at least 1 mm.

12. The system according to claim 1, wherein the first and the second muon detector are at least 12 square meters each.

13. The system according to claim 1, wherein an alarm system is adapted to produce a sound when the difference between the predicted second incidence angle and the actual second incidence angle exceeds a predetermined value.

14. The system according to claim 1, further comprising a density of a substance between the first and the second detector changing in time, when the nuclear material is in a vehicle moving along the detectors with a speed V, wherein the detectors size assures measurement of at least one muon trajectory in each square of 100 cm.sup.2 of the vehicle.

15. The system according to claim 1, wherein the first and the second muon detectors are gas chambers with at least one wire grid in each.

16. The system according to claim 1, wherein the second detector is a scintillation detector.

17. The system of claim 1, wherein at least the second detector is adapted to be positioned under ground.

18. A method for nuclear material revealing, comprising the steps of:
   selecting muons from other charged particles, continuously measuring a first coordinate and a first incident angle of incoming muons by a first detector, estimating a predicted second coordinate and a predicted second incidence angle at a second detector for each incoming muon, continuously measuring an actual second coordinate and an actual second incidence angle for each incoming muon by the second detector, comparing the actual second coordinate and the actual second incidence angle with the predicted second coordinate and the predicted second incidence angle for each muon, producing an alarm signal if a difference between the predicted second incidence and the actual second incidence angle exceeds a predetermined value, further comprising chemical substance detecting, including:

emitting a first light beam having one or more wavelengths, the first beam interacting with the chemical and changing a refractive index of the chemical; emitting a second light beam, the second beam interacting with the chemical resulting in a third light beam with a phase change that corresponds with the change of the refractive index of the chemical; detecting at least a portion of the third beam, recovering information on a phase change in the third beam relative to the second beam that is indicative of at least one of absorption spectrum and concentration of the chemical.

19. The method of claim 18, further comprising: continuously measuring an actual second coordinate and an actual second incidence angle for each incoming muon by a third muon detector and a fourth muon detector, wherein the third muon and the fourth muon detectors are essentially perpendicular to the first and second detectors.

20. The method of claim 18, wherein the first and the second muon detectors are gas chambers with at least one wire grid in each.

* * * * *